(12) United States Patent
Jin et al.

(10) Patent No.: US 7,311,194 B2
(45) Date of Patent: Dec. 25, 2007

(54) LENS MOUNTING FIXTURE FOR ACCOMMODATING IOL

(75) Inventors: Wen X. Jin, Victor, NY (US); Charles P. Henning, Rochester, NY (US); Larry C. Hovey, Ontario, NY (US); Ted Foos, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 415 days.

(21) Appl. No.: 10/747,609

(22) Filed: Dec. 29, 2003

(65) Prior Publication Data

US 2005/0143815 A1    Jun. 30, 2005

(51) Int. Cl.
B65D 81/18    (2006.01)
B65D 81/24    (2006.01)

(52) U.S. Cl. .................. 206/5.1; 206/477; 206/210; 206/775

(58) Field of Classification Search ............... 451/390; 206/5.1, 210, 477, 775; 623/6.37, 6.46, 6.12, 623/6.4, 6.38; 606/107
See application file for complete search history.

(56) References Cited

U.S. PATENT DOCUMENTS

| | | | |
|---|---|---|---|
| 4,104,339 A | 8/1978 | Fetz et al. | |
| 4,173,281 A | 11/1979 | Trought | |
| 4,205,747 A | 6/1980 | Gilliam et al. | |
| 4,257,521 A | 3/1981 | Poler | |
| 4,269,307 A | * 5/1981 | LaHaye | 206/5.1 |
| 4,402,396 A | * 9/1983 | Graham | 206/5.1 |
| 4,423,809 A | 1/1984 | Mazzocco | |
| 4,508,216 A | 4/1985 | Kelman | |
| 4,615,703 A | * 10/1986 | Callahan et al. | 623/66.1 |
| 4,684,014 A | 8/1987 | Davenport | |
| 4,697,697 A | 10/1987 | Graham et al. | |
| 4,736,836 A | 4/1988 | Alongi et al. | |
| 4,817,789 A | 4/1989 | Paul | |
| 4,844,242 A | 7/1989 | Chen et al. | |
| 4,897,981 A | 2/1990 | Beck | |
| 4,928,815 A | 5/1990 | Paul | |
| 5,176,686 A | 1/1993 | Poley | |

(Continued)

FOREIGN PATENT DOCUMENTS

JP    2001346817    12/2001

(Continued)

OTHER PUBLICATIONS

Hovey, et al., "Universal Accommodating IOL Holder for Lens Processing and Packaging," U.S. Appl. No. 10/747,393, filed Dec. 29, 2003.

(Continued)

*Primary Examiner*—Joseph J. Hail, III
*Assistant Examiner*—Robert Scruggs
(74) *Attorney, Agent, or Firm*—Jeffrey B. Powers

(57) ABSTRACT

The present invention provides a fixture for supporting a two optic accommodating intraocular lens device. The fixture is capable of holding the device while taking measurements or performing manufacturing process steps on the device. In a preferred embodiment, the fixture supports the device along the periphery of the posterior optic thereof such that the haptics and anterior optic extend freely therefrom. As such, testing and/or processing of the optics during their accommodative and unaccomodative positions may be taken.

16 Claims, 4 Drawing Sheets

U.S. PATENT DOCUMENTS

| | | |
|---|---|---|
| 5,257,521 A | 11/1993 | Castricum |
| 5,275,623 A | 1/1994 | Sarfarazi |
| 5,281,227 A | 1/1994 | Sussman |
| 5,549,614 A * | 8/1996 | Tunis .................... 606/107 |
| 5,556,400 A | 9/1996 | Tunis |
| 5,589,024 A | 12/1996 | Blake |
| 5,674,284 A | 10/1997 | Chang et al. |
| 6,183,513 B1 | 2/2001 | Guenthner et al. |
| 6,360,883 B1 | 3/2002 | Haq et al. |
| 6,386,357 B1 | 5/2002 | Egawa |
| 6,423,094 B1 | 7/2002 | Sarfarazi |
| 6,488,708 B2 * | 12/2002 | Sarfarazi .................... 623/6.34 |
| 6,797,004 B1 * | 9/2004 | Brady et al. ................. 623/6.4 |
| 2003/0078658 A1 | 4/2003 | Zadno-Azizi |
| 2003/0209452 A1 | 11/2003 | Mitomo et al. |
| 2003/0214139 A1 | 11/2003 | Nigam |
| 2004/0238980 A1 | 12/2004 | Sarfarazi et al. |
| 2005/0143813 A1 | 6/2005 | Hovey et al. |
| 2006/0037871 A1 | 2/2006 | Jin et al. |

FOREIGN PATENT DOCUMENTS

| | | |
|---|---|---|
| JP | 2002/102261 | 4/2002 |
| WO | WO 00/61036 A1 | 10/2000 |
| WO | WO 02/071983 A1 | 9/2002 |
| WO | WO 02/096322 A1 | 12/2002 |
| WO | WO 02/098327 A1 | 12/2002 |
| WO | WO 03/045285 A1 | 6/2003 |
| WO | WO 2005-065590 A1 | 7/2005 |
| WO | WO 2006/023682 A2 | 3/2006 |

OTHER PUBLICATIONS

Jin et al., "U.S. Appl. No. 10/920,623 Entitled "Holder for Dual Optic IOL" filed Aug. 18, 2004,".

Sarfarazi et al., "U.S. Appl. No. 10/445,762 Entitled "Mold for Intraocular Lens" filed May 27, 2003,".

* cited by examiner

LENS MOUNTING FIXTURE FOR ACCOMMODATING IOL

BACKGROUND OF THE INVENTION

The present invention relates to optical lens holders used for performing tests or other processes on the lens. More particularly, the present invention relates to a holder for supporting an accommodating intraocular lens device having at least two optics interconnected by one or more haptics.

Intraocular lenses having a single optic have been known and used for many years. More recently, accommodating intraocular lens devices having two optics interconnected by one or more haptics have been disclosed in the following U.S. patents and applications to Faezeh Sarfarazi, the entirety of which are incorporated herein by reference:

U.S. Pat. No. 5,275,623 "Elliptical Accommodative Intraocular Lens For Small Incision Surgery";
U.S. Pat. No. 6,423,094 "Accommodative Lens Formed From Sheet Material";
U.S. Pat. No. 6,488,708 "Open Chamber Elliptical Accommodative Intraocular Lens System";
U.S. Ser. No. 10/445,762 filed on May 27, 2003 entitled "Mold for Intraocular Lens".

The Sarfarazi accommodating lens device includes two optics, one negative and the other positive for placing in the evacuated lens capsule of an eye. The optics are interconnected along their peripheries by one or more haptics which space the optics from each other and assist in properly positioning the device in the eye. The haptics are formed from a flexible material such that they may flex in response to forces exerted by the eye's ciliary muscles which control accommodation. The haptics will thus flex and bow further radially outwardly upon a compressive force being applied to the device, whereby the two optics are drawn closer together to achieve an accommodative effect in the eye. When the ciliary muscles relax, the haptics flex in the opposite direction (toward a straightened positioned) causing the optics to space further apart and the lens device returns the eye to its natural, unaccommodative state.

As stated above, single optic intraocular lenses have been known and used for decades while the two lens accommodative intraocular lens device is new and not yet seen on the market. It will be appreciated that manufacturing a two optic lens device presents issues not present in the manufacture of single optic intraocular lenses. During design and manufacture of intraocular lenses, certain measurements must be taken of the device to ensure the device achieves its design parameters. Certain measurements require not only that the device be held stationary, but also not interfere with the optic pathway. Furthermore, in a two optic device, the optics must be able to be moved in a manner simulating their accommodative movements in the eye. The holder for such a device must therefore be able to hold the device stationary while also allowing relative movement of the optics. Besides the taking of measurements, manufacturing process steps may need to be carried out such as polishing, for example. The holder should therefore also be able to support the device during manufacturing process steps without damage to the device.

SUMMARY OF THE INVENTION

The present invention provides a holder for supporting a two optic accommodating intraocular lens device. The holder is capable of holding the device while taking measurements or performing manufacturing process steps on the device. In a preferred embodiment, the holder supports the posterior optic periphery with the haptics and anterior optic extending freely therefrom and untouched by the holder. As such, testing and/or processing of the optics during their accommodative and unaccomodative positions may be taken.

The holder includes a fixture having at least one but preferably three lens holding elements attached to the fixture, whereby the intraocular lens device may be removably attached to the holder by engaging the periphery of the posterior optic on the lens holding elements of the fixture. The lens holding elements may be integrally formed with the fixture or attached separately to the fixture. The lens holding elements each include a radial inward projection which together at their inward edges define an opening having a diameter slightly smaller than the outer diameter of the lens optic. As such, the optic periphery may be pressed past the projections onto the fixture and thereby allow the intraocular lens device to be alternately mounted and dismounted from the holder. The amount of deformation required for the optic periphery to pass the projections is small enough so as to not damage the lens. When the intraocular lens device is supported on the holder, the posterior optic rests on the fixture with the anterior optic thereof spaced above and parallel to the posterior optic whereby the anterior optic may be moved relative to the posterior optic when performing tests thereon.

DETAILED DESCRIPTION

Figure 1A:
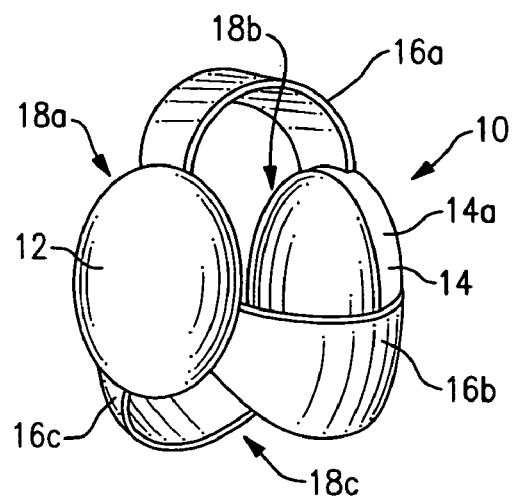
FIG. 1A is a perspective view of an embodiment of an accommodative intraocular lens which may be supported by the holder of the present invention.
Figure 1B:
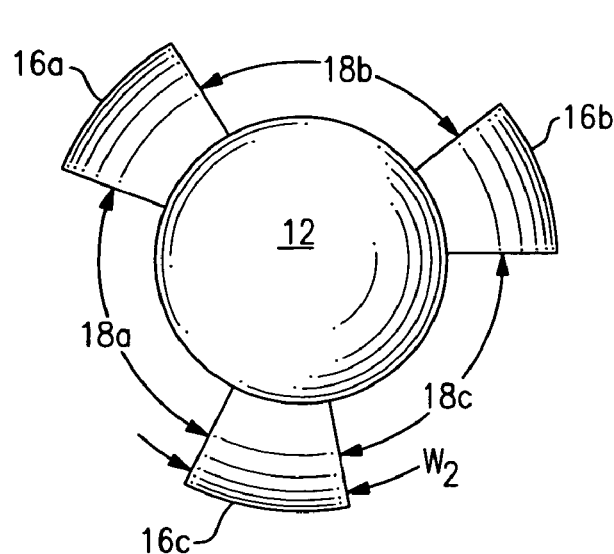
FIG. 1B is a plan view thereof.
Figure 1C:
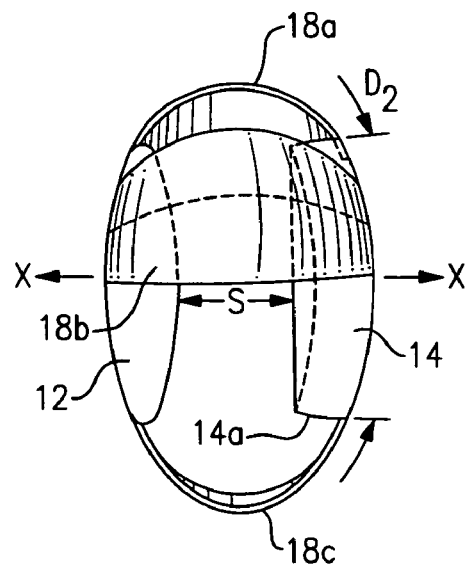
FIG. 1C is a side elevational view thereof.

Referring now to the drawing, there is seen in FIGS. 1A-C a representative embodiment of an accommodative intraocular device 10 which may be supported by the present invention. Briefly, lens device 10 includes first and second optics 12, 14 interconnected by one or more, but preferably three haptics 16a, 16b and 16c defining three open spaces 18a, 18b, 18c therebetween, respectively. Haptics 16a-c bow outwardly past the optic perimeters 12p, 14p and are flexible whereby the optics may move alternately toward and away from each other generally along the optical axis x-x. Optics 12, 14 are preferably flexible and may be made of any suitable IOL lens material. FIGS. 1A and 1C show the space "S" between the optics 12, 14 which gets smaller as the optics move toward one another and larger as the optics move away from one another. It is understood that the present invention is a holder for a lens device and therefore the particular optic and haptic configurations of a lens device which may be supported by the inventive holder may vary from that shown and described herein.

Figure 2A:
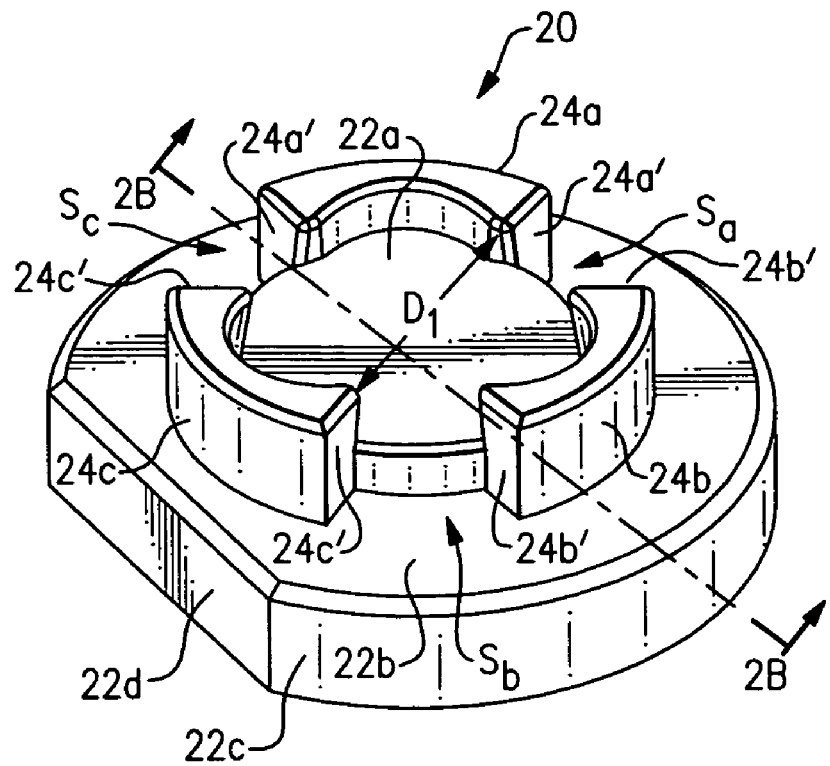
FIG. 2A is a perspective view of a first embodiment of the inventive fixture.
Figure 2B:
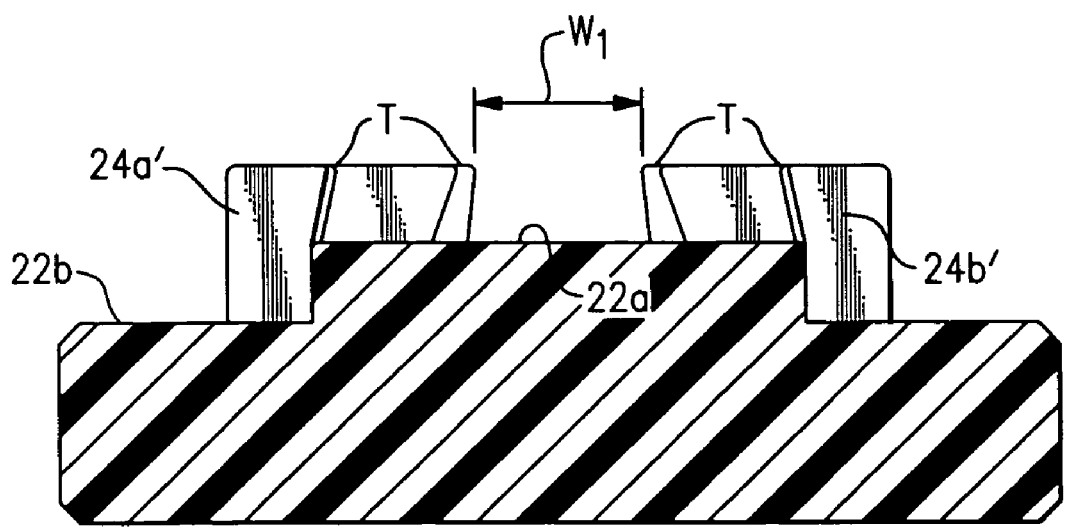
FIG. 2B is a cross-sectional view as taken along the line 2B-2B in FIG. 2A.

Turning to FIG. 2, a first embodiment of the fixture is indicated generally by reference numeral 20. Fixture 20 includes a central support surface 22a surrounded by at least one, but preferably three annularly spaced lens holding elements 24a, 24b and 24c. In the preferred embodiment, support surface 22a is circular and may be raised relative to outlying subsurface 22b. The lens holding elements 24a-c thus define three spaces Sa, Sb and Sc therebetween wherein the haptics 16a-c of lens element 10 are positioned. In this regard, it is noted that the width $W_1$ (FIG. 2B) of spaces Sa-c needs to be slightly larger than the haptic width $W_2$ (FIG. 1B) to allow the haptics 16a-c to pass freely within the spaces Sa-c defined between the lens holding elements 24a-c, respectively.

Figure 3:
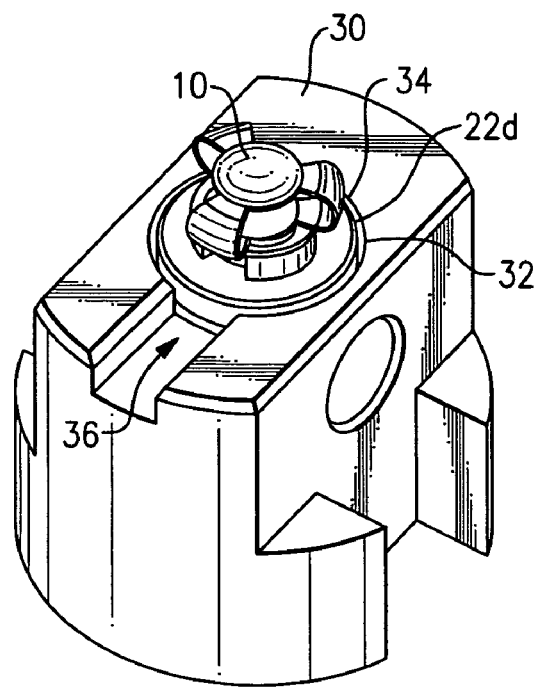
FIG. 3 is a perspective view of the fixture of FIGS. 2A,B positioned in a horizontal fixture holder.
Figure 4:
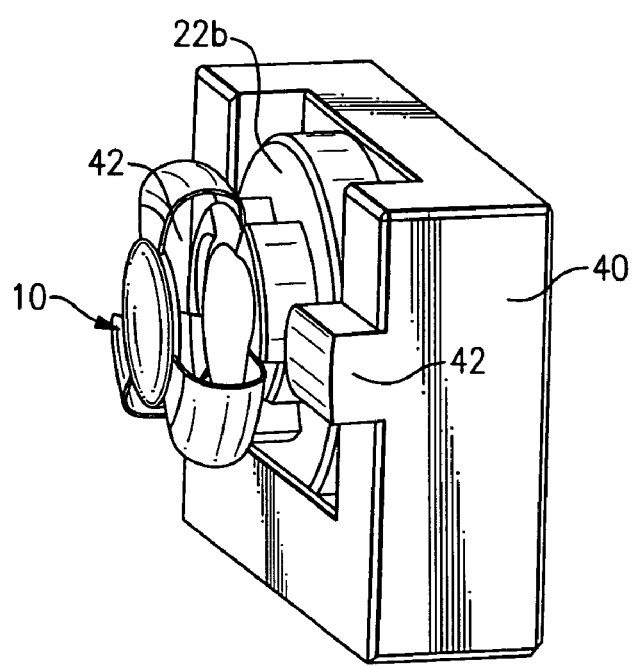
FIG. 4 is a perspective view of the fixture of FIGS. 2A,B positioned in a vertical fixture holder.

In the embodiment of FIGS. 2A, 2B, each lens holding element 24a-c is itself annularly curved about support surface 22a with the outermost ends 24a'-c' thereof having a dovetail shape. Diametrically opposed inner-most tips "T" of the lens holding elements define a diameter $D_1$ (FIG. 2A) which is slightly smaller than the outermost diameter $D_2$ (FIG. 1C) of the posterior optic 14. As such, the peripheral edge 14a of posterior optic 14 may be safely pressed past the inner most tips "T" of the dovetail until the posterior optic 14 is seated upon surface 22a. The dovetail shape of the lens holding elements secure the optic 14 to the fixture and thus the entire lens device 10 is held securely thereby as seen in FIGS. 3 and 4. In this secured condition, the haptics 16a-c and anterior optic 12 extend freely upward from the captured posterior optic 14. It is noted that although it is preferred to secure the posterior optic on surface 22a, the lens device 10 may be inverted with the anterior optic 12 instead secured thereby.

Referring still to FIGS. 3 and 4, fixture 20 may further include means for removably mounting fixture 20 to a fixture holder 30 which itself may be removably mounted to other testing and/or processing equipment such as an optical bench, for example (not shown). The fixture holder 30 includes a circular recess 32 wherein the circumference of fixture support side wall 22c may fit. Cooperative flats 22d and 34 (FIGS. 2A and 3) on the fixture 20 and fixture holder 30, respectively, may be provided for establishing the correct rotational position of the fixture within the holder. A slot 36 may extend from recess 32 for access by a tweezer or other tool to assist in loading and unloading the fixture 20 from the fixture holder 30. It will be appreciated that by making the fixture 20 and fixture holder 30 removably mountable to other equipment, the fixture 20 may be conveniently moved from one work station to another when performing different tests or processes on the lens device 10.

Referring to FIG. 4, another embodiment of fixture holder is indicated by reference numeral 40. The main difference between fixture holder 30 and fixture holder 40 is that holder 30 is designed to hold the lens device in a horizontal orientation while holder 40 is designed to hold the lens device 10 in a vertical orientation. The vertical positioning of fixture 20 and lens device 10 is achieved in holder 40 by a pair of side arms 42 which engage the top surface of outlying support surface 22b. In the horizontal orientation of FIG. 3 a vertical compression force may be applied to anterior optic 12 (normal to anterior optic 12) to flex the haptics 16a-c and thereby mimic accommodation of the device 10 for testing purposes. In the vertical orientation of FIG. 4, a horizontal compression force may be applied against anterior optic 12 (again normal to anterior optic 14) to flex haptics 16a-c and thereby mimic accommodation of the device 10 for testing purposes.

Figure 5:
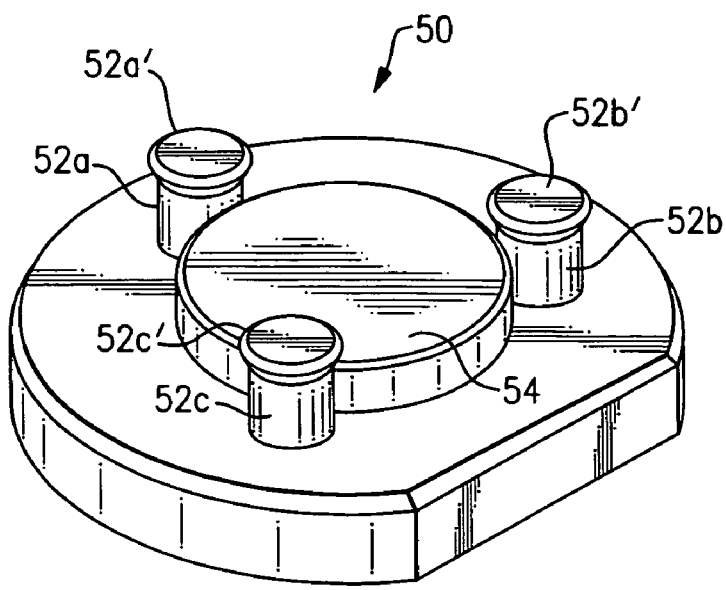
FIG. 5 is perspective view an a second embodiment of the inventive fixture.
Figure 6:
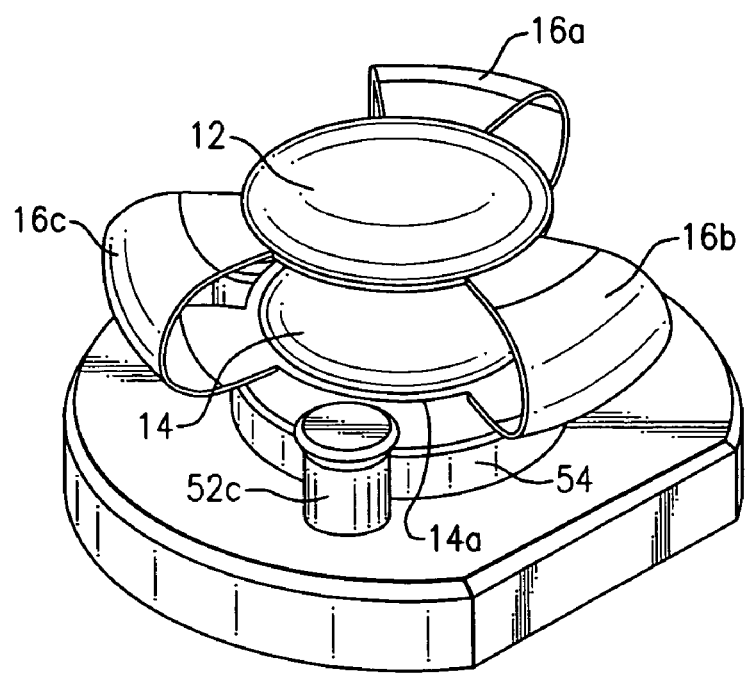
FIG. 6 is the view of FIG. 5 showing an accommodating IOL positioned on the fixture in the intended manner.

FIGS. 5 and 6 show another embodiment of the fixture indicated by the reference numeral 50. Fixture 50 is similar to fixture 20 with the difference being the shape of the lens holding elements. In fixture 50, the lens holding elements are shaped as pinions 52a-c each having a top cap 52a'-c'. The periphery 14a of the posterior optic 14 may be safely pressed past the caps 52a'-c' to seat posterior optic 14 on support surface 54 with the haptics 16a-c extending in between the pinions 52a-c as seen in FIG. 6. It is thus understood that the fixture holder may take a variety of configurations and the invention is not to be limited to the exact configuration shown and described herein.

What is claimed is:

1. An intraocular lens assembly, comprising:
   I. an intraocular lens device having first and second optics interconnected by a plurality of haptics, one of the first and second optics having a diameter $D_2$; and
   II. a fixture comprising
       a) a support surface;
       b) a plurality of lens holding elements coupled to said support surface each having a feature, said features forming an innermost diameter $D_1$ that is less than $D_2$, said holding elements being spaced about said one of said first and second optics such that said haptics freely pass between said features, whereby said intraocular lens device is removably attached to said fixture by securing only said one of said optics with said features.

2. The assembly of claim 1 wherein said lens holding elements are annularly curved and spaced about the perimeter of said support surface, and said features comprise tips of said holding elements.

3. The assembly of claim 2 wherein said lens holding elements have a dove-tail shape.

4. The assembly of claim 3 wherein two diametrically opposed tips define diameter $D_1$ whereby said optic may be pressed past said tips and thereby secured by said fixture.

5. The assembly of claim 1 further comprising a fixture holder and a subsurface surrounding said support surface for removably mounting said fixture to said fixture holder.

6. The assembly of claim 5 wherein said fixture and said fixture holder have cooperative flats for fixing the rotational orientation therebetween when said fixture is removably mounted to said fixture holder.

7. The assembly of claim 1 wherein said lens holding elements are configured as pinions each having a top cap.

8. The assembly of claim 7 wherein the distance between two diametrically opposed pinions define diameter $D_1$ whereby said one of said first and second optics may be pressed past said top caps and thereby be secured to said fixture.

9. The assembly of claim 7 wherein said support surface is circular and said lens holding elements are spaced about the perimeter of said support surface.

10. The assembly of claim 7 further comprising a fixture holder and a subsurface surrounding said support surface for removably mounting said fixture to said fixture holder.

11. The assembly of claim 10 wherein said fixture and said fixture holder have cooperative flats for fixing the rotational orientation therebetween when said fixture is removably mounted to said fixture holder.

12. The assembly of claim 1, wherein the first and second optics are spaced apart from one another.

13. The assembly of claim 1, wherein the plurality of holding elements comprise at least three holding elements.

14. The assembly of claim 1, wherein the plurality of holding elements consist of three holding elements.

15. The assembly of claim 1, wherein said one of the first and second optics is a posterior optic.

16. The assembly of claim 1, wherein said one of the first and second optics is an anterior optic.

* * * * *